United States Patent
Asako et al.

(10) Patent No.: US 7,135,318 B2
(45) Date of Patent: Nov. 14, 2006

(54) MODIFIED REDUCTASE AND ITS GENE

(75) Inventors: Hiroyuki Asako, Toyonaka (JP); Masatoshi Shimizu, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 417 days.

(21) Appl. No.: 10/608,533

(22) Filed: Jun. 30, 2003

(65) Prior Publication Data

US 2004/0091902 A1    May 13, 2004

(30) Foreign Application Priority Data

Jul. 2, 2002    (JP)    ............. 2002-193074

(51) Int. Cl.
C12N 9/02 (2006.01)
C12N 15/00 (2006.01)
C12Q 1/00 (2006.01)
C12Q 1/68 (2006.01)
C12Q 1/26 (2006.01)
C12P 21/04 (2006.01)
C07H 21/04 (2006.01)

(52) U.S. Cl. .................. 435/189; 435/440; 435/4; 435/6; 435/69.1; 435/25; 536/23.2; 536/23.7

(58) Field of Classification Search .......... 435/189, 435/440, 252.3, 320.1, 69.1, 4, 6, 71.1, 25; 536/23.2, 23.7
See application file for complete search history.

(56) References Cited

U.S. PATENT DOCUMENTS

| 4,455,373 A | 6/1984 | Higgins |
| 4,895,979 A | 1/1990 | Noyori et al. |
| 5,215,919 A | 6/1993 | Miya et al. |
| 5,233,095 A | 8/1993 | Fellmann et al. |
| 5,908,953 A | 6/1999 | Matsuda et al. |
| 6,218,156 B1 | 4/2001 | Yasohara et al. |
| 6,312,933 B1 | 11/2001 | Kimoto et al. |
| 2003/0134402 A1 | 7/2003 | Asako et al. |
| 2003/0186400 A1 | 10/2003 | Asako et al. |

FOREIGN PATENT DOCUMENTS

| EP | 0 400 239 A1 | 12/1990 |
| EP | 0 967 271 A1 | 12/1999 |
| EP | 1 013 758 A2 | 6/2000 |
| EP | 1 201 647 A2 | 5/2002 |
| EP | 1 213 354 A2 | 6/2002 |
| JP | 60-251890 A | 12/1985 |
| JP | 63-123387 A | 5/1988 |
| JP | 01-222787 A | 9/1989 |
| JP | 02-312593 A | 12/1990 |
| JP | 2532299 B2 | 6/1996 |
| JP | 2566962 B2 | 10/1996 |
| JP | 10-94399 A | 4/1998 |
| JP | 2001-294549 A | 10/2001 |

OTHER PUBLICATIONS

U.S. Appl. No. 10/608,625 to Asako et al., filed Jun. 30, 2003.
U.S. Appl. No. 10/617,034 to Itoh et al., filed Jul. 11, 2003.
Itoh et al., "Chiral alcohol production by NADH-dependent phenylacetaldehyde reductase coupled with in situ regeneration of NADA," Eur. J. Biochem. 269, 2002, pp. 2394-2402.
Nakamura et al., "Recent developments in asymmetric reduction of ketones with biocatalysts", Tetrahedron: Asymmetry Report No. 60, Tetrahedron: asymmetry, 14, (2003), pp. 2659-2681.
Spiliotis et al., "Enhanced Optical Purity of 3-Hydroxyesters Obtained by Baker's Yeast Reduction of 3-Ketoesters", Tetrahedron Letters, vol. 31, No. 11, 1990, pp. 1615-1616.
Wei et al., "Baker's yeast mediated mono-reduction of 1,3-cyclohexanediones bearing two identical C(2) substituents", Tetrahedron: Asymmetry, vol. 12, 2001, pp. 229-233.
N. Itoh et al., "Chiral alcohol production by β-ketoester reductase from Penicillium citrinum coupled with regeneration system of NADPH", Journal of Molecular Catalysis B Enzymatic, vol. 22, No. 3-4, Jun. 2, 2003, pp. 247-248.
Itoh et al., "Production of chiral alcohols by enantioselective reduction with NADH-dependent phenylacetaldehyde reductase from Corynebacterium stain, ST-10", Journal of Molecular Catalysis B: Enzymatic, vol. 6, 1999, pp. 41-50.
Itoh et al., "Purification and Characterization of Phenylacetaldehyde Reductase from a Styrene-Assimilating Corynebacterium Strain, ST-10", Applied and Environmental Microbiology, vol. 63, No. 10, Oct. 1997, pp. 3783-3788.
Wang et al., "Cloning, sequence analysis, and expression in Escherichia coli of the gene encoding phenyklacetaldehyde reductase from styrene-assimilating Corynebacterium sp. Strain ST-10", Applied Microbiology Biotechnology, vol. 52, 1999, pp. 386-392.

(Continued)

Primary Examiner—Tekchand Saidha
Assistant Examiner—Yong D. Pak
(74) Attorney, Agent, or Firm—Sughrue Mion, PLLC

(57) ABSTRACT

There are disclosed a reductase having good heat stability, which resulted in decrease in reaction time and improvement of reaction efficiency. Specifically, disclosed is an enzyme having an amino acid sequence of SEQ ID NO:1 in which at least one of the amino acids of the positions 245 and 271 of the amino acid sequence of SEQ ID NO:1 is replaced with another amino acid(s); a polynucleotide having a nucleotide sequence that encodes the amino acid sequence of said reductase; a vector containing said polynucleotide; a transformant containing said polynucleotide or said vector, and the like.

2 Claims, No Drawings

OTHER PUBLICATIONS

Itoh et al., "1465. Chiral alcohols production by enantioselective reduction with NADH-dependent phenylacetaldehyde reductase (PAR)", *Book of Abstracts, 2000 International Chemical Congress of Pacific Basin Societies*, Dec. 14-19, 2000, p. 9.

Itoh et al., "3Y7p7. Production of optically active alcohol by using a phenylacetaldehyde reductase (PAR) recombinant strain", *Nippon Nogeikagaku Kaishi*, vol. 75, Mar. 5, 2001, with translation of 3Y7P7.

Itoh et al., "3F302β. Analysis of the phenylacetaldehyde reductase (PAR) gene from styrene-assimilating *Corynebacterium*", *Nippon Nogeikagaku Kaishi*, vol. 74, Mar. 5, 2000, with translation of 3F302β.

Itoh et al., "3F303α. Production of optically active alcohol by using the phenylacetaldehyde reductase (PAR) from *Corynebhacterium* sp. ST10", *Nippon Nogeikagaku Kaishi*, vol. 74, Mar. 5, 2000, with translation of 3F303α.

Asako et al., "P214. Chiral Alcohol Production by β-Ketoester Reductase from *Penicillum citrinum* Coupled with Regeneration System of NADPH", *Chem. Litsy 97*, 6th International Symposium on Biocatalysis and Biotransformation, Jun. 28-Jul. 3, 2003, p. 489.

Lecture Summary Series of the 6th Organism Catalyst Chemistry Symposium, Dec. 12-13, 2002, p. 70, with partial English translation.

Conference Lecture Summary Series, published Mar. 5, 2003, 3A11a01, with partial English translation.

US 7,135,318 B2

MODIFIED REDUCTASE AND ITS GENE

FIELD OF THE INVENTION

The present invention relates to a modified reductase that can be used for reduction reaction, specifically reduction reaction of β-keto acid, and the like, and its gene and use thereof.

The present invention relates to a modified reductase having heat stability, a gene required to produce the reductase and a vector comprising said gene, a transformant comprising said vector, and a production method for the modified reductase using said transformant.

BACKGROUND OF THE INVENTION

Reductases reduce unsaturated organic compounds, and have been used recently in an organic synthesis reaction for producing compounds that are used as active ingredients of medicaments or agrochemicals or intermediates thereof, especially for the production of optically active compounds.

According to the present invention, there is provided a modified reductase comprising an amino acid substitution(s) at certain amino acid residue(s) in a wild-type reductase amino acid sequence, thereby heat stability of the reductase is improved.

The present invention provides:

1) a reductase comprising
   i) an amino acid sequence of SEQ ID NO:1 having a substitution at amino acid position 245 or 271 or at both of the amino acid positions 245 and 271, or
   ii) an amino acid sequence as defined in i) having further substitution, deletion, or addition of an amino acid or acids;
2) a reductase according to 1) above, which comprises an amino acid sequence of SEQ ID NO:1 having a substitution at amino acid position 245 or 271 or at both of the amino acid positions 245 and 271;
3) a reductase according to 1) or 2) above, wherein said substitution is a single amino acid substitution at amino acid position 245 of the amino acid sequence of SEQ ID NO:1;
4) a reductase according to 1) or 2) above, wherein said substitution is a single amino acid substitution at amino acid position 271 of the amino acid sequence of SEQ ID NO:1;
5) a reductase according to 1) or 2) above, wherein the amino acids at positions 245 and 271 of the amino acid sequence of SEQ ID NO:1 are substituted with a same amino acid or different amino acids;
6) a reductase according to 3) or 5) above, wherein the amino acid at amino acid position 245 is substituted with arginine;
7) a reductase according to 4) or 5) above, wherein the amino acid at amino acid position 271 is substituted with aspartic acid;
8) a reductase according to 1) above, wherein the amino acid at amino acid position 245 of the amino acid sequence of SEQ ID NO:1 is substituted with arginine, and the amino acid at amino acid position 271 of the amino acid sequence of SEQ ID NO:1 is substituted with aspartic acid;
9) a polynucleotide sequence comprising a polynucleotide sequence encoding an amino acid sequence of the reductase of 1) or 2) above;
10) a vector comprising the polynucleotide of 9) above;
11) a transformant comprising the polynucleotide sequence of 9) above or the vector of 10) above;
12) a vector according to 10) above, which further comprises a polynucleotide sequence encoding an amino acid sequence of a protein capable of converting an NADP or an NAD into NADPH or NADH respectively;
13) a transformant of 11) above, which further comprises a polynucleotide sequence encoding the amino acid sequence of a protein capable of converting an NADP or NAD into NADPH or NADH respectively;
14) a method for producing (S)-halo-3-hydroxybutyrate ester, which comprises reacting 4-halo-3-oxobutyrate ester with the transformant of 11) or 13) above or a treated material thereof;
15) a method for modifying an enzyme, which comprises replacing at least one of the amino acids at positions 245 and 271 of the amino acid sequence of SEQ ID NO:1 respectively with another amino acid(s), thereby heat stability of said enzyme in the reduction reaction is improved; and
16) a method for producing a modified enzyme gene, which comprises replacing at least one codon corresponding to the amino acids at positions 245 and 271 of the amino acid sequence of SEQ ID NO:1, with another codon or codons corresponding to an amino acid(s), in a nucleotide sequence encoding the amino acid sequence of SEQ ID NO:1.

DETAILED DESCRIPTION OF THE INVENTION

Hereinafter the present invention is explained in more detail.

The present invention concerns a protein that comprises the sequence SEQ ID NO: 1 but has a substitution(s) at positions 245 and/or 271 of SEQ ID NO: 1. The region corresponding to SEQ ID NO: 1 in the protein may comprise further changes (deletions and/or substitutions and/or additions). Thus the protein will comprise a region which is homologous to SEQ ID NO: 1. Preferably proteins of the invention comprising such homologous regions will retain reductase activity.

The homologous sequence typically has at least 70% homology, preferably at least 80%. 90%, 95%, 97% or 99% homology, for example over a region of at least 30, 100, 200 or more contiguous amino acids, such as over the entire length of SEQ ID NO: 1. The homology may be calculated on the basis of amino acid identity (sometimes referred to as "hard homology").

For example the UWGCG Package provides the BEST-FIT program which can be used to calculate homology (for example used on its default settings) (Devereux el al (1984) Nucleic Acids Research 12, p387–395). The PILEUP and BLAST algorithms can be used to calculate homology or line up sequences (such as identifying equivalent or corresponding sequences (typically on their default settings)), for example as described in Altschul S. F. (1993) J Mol Evol 3 6:290–300: Altschul, S, F et al (1990). J Mol Biol 215: 403–10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value: the cumulative score goes to zero or below, due to the accumulation of one or more negative-scoring residue alignments: or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc, Natl. Acad. Sci.* USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two amino acid sequences would occur by chance, For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs from SEQ ID NO: 1 by less than 100 mutations, such as less than 70, less than 50, less than 30 or less than 15 mutations (each of which may be a substitution, deletion or addition of an amino acid).

The reductase having the amino acid sequence of SEQ ID NO:1 (hereinafter referred to as a wild-type reductase) is a reductase derived from *Penicillium citrinum* IFO4631 strain (available from the Institute for Fermentation, Osaka (www.ifo.or.jp)). The activity of the reductase of the strain or the reductase of the present invention (i.e. ability to reduce a substrate) can be measured by mixing each reductase with, for example, methyl 4-bromo-3-oxobutyrate and NADPH, keeping the resulting mixture at 30° C., and determining the amount of the liberated NADP$^+$ using the absorbance of the reaction solution at 340 nm as an index. In the present invention, the "heat stability" means that the residual percentage of the activity after being maintained at 45° C. for 7 hr is higher than that of the wild-type reductase treated in the same manner.

In order to obtain a gene having a nucleotide sequence that encodes the amino acid sequence of the reductase of the present invention (hereinafter referred to as the gene of the present invention), the first step is typically to obtain a gene having a nucleotide sequence that encodes an amino acid sequence of the wild-type reductase (hereinafter referred to as the "wild-type gene"). The wild-type gene is, for example, a gene having a nucleotide sequence of SEQ ID NO:2, and it can be obtained from *Penicillium citrinum* IFO4631 strain according to a procedure usually employed of gene engineering as described in, for example, J. Sambrook, E. F. Fritsch, T. Maniatis ed., Molecular Cloning 2nd Edition, Cold Spring Harbor Laboratory, 1989 and the like.

That is, the reductase gene of the present invention may be prepared, for example, by preparing a cDNA library according to a method described in "New Cell Technology Experimental Protocol" (Division of Oncology, Institute of Medical Science, University of Tokyo ed. Shujunsha Co., Ltd, 1993) from *Penicillium citrinum* IFO4631 strain and conducting PCR using the prepared cDNA library as a template and a suitable primer to amplify any one of the following DNA: a DNA comprising a nucleotide sequence that encodes the amino acid sequence of SEQ ID NO:1, a DNA comprising a nucleotide sequence that encodes an amino acid sequence of SEQ ID NO:1 with one or more deletion, substitution or addition of amino acid(s), or a DNA having the nucleotide sequence of SEQ ID NO:2.

When PCR is conducted using the cDNA library derived from *Penicillium citrinum* as a template and using an oligonucleotide having the nucleotide sequence of SEQ ID NO:3 and an oligonucleotide having the nucleotide sequence of SEQ ID NO:4 as primers, the reductase gene of the present invention is prepared by amplifying the DNA consisting of the nucleotide sequence of SEQ ID NO:2.

In the present invention, an amino acid sequence equivalent to the amino acid sequence of the wild-type reductase means the amino acid sequence of SEQ ID NO:1 or the amino acid sequence substantially identical to that sequence comprising deletion, addition, substitution of up to several amino acids(i.e., equivalent sequence). As used herein, the "substitution" means a substitution of an amino acid residue(s) in the wild-type reductase with an amino acid residue(s) having similar characteristics with respect to hydrophobicity, electron charge, pK, characteristics of the steric structure and the like, and such substitution includes a substitution within the respective groups of (1) glycine, and alanine; (2) valine, isoleucine, and leucine; (3) aspartic acid, glutamic acid, asparagine, and glutamine; (4) serine, and threonine; (5) lysine, and arginine; and (6) phenylalanine, and tyrosine.

The gene of the present invention can be prepared by introducing site-specific mutation into the wild-type gene. The methods for introducing site-specific mutation include methods of, for example, Olfert Landt et al. (Gene 96 125–128 1990), Smith et al. (Genetic Engineering 3 1 Setlow, J. and Hollaender, A Plenum: New York), Vlasuk et al. (Experimental Manipulation of Gene Expression, Inouye, M.: Academic Press, N.Y.), Hos. N. Hunt et al. (Gene 77 51 1989), or utilization of commercial kits such as Mutan-Express Km (manufactured by Takara Shuzo Co., Ltd.), TaKaRa La PCR in vitro Mutagenesis Kit (manufactured by Takara Shuzo Co., Ltd.), and the like.

For example, in order to prepare the gene of the present invention that encodes the amino acid sequence of SEQ ID NO:1 with substitution of an amino acid at the amino acid position 245 using the method by Olfert Landt et al. (Gene 96 125–128 1990), the vector DNA comprising the wild-type gene having the nucleotide sequence of SEQ ID NO:2 is prepared first, for example, according to the methods described in J. Sambrook, E. F. Fritsch, T. Maniatis ed.; Molecular Cloning 2nd edition, Cold Spring Harbor Laboratory, 1989 and the like. Then the resulting DNA fragment may be amplified by PCR method using the obtained vector DNA as a template, for example, using an oligonucleotide comprising a nucleotide sequence that encodes the amino acid sequence of SEQ ID NO:1 having a substitution of an amino acid at position 245(e.g., an oligonucleotide having the nucleotide sequence of SEQ ID NO:5) as one primer and an oligonucleotide having the nucleotide sequence of SEQ ID NO:6 as the other primer. The condition of the PCR comprises, for example, 1) repeating a cycle comprising keeping at 94° C. for 5 min, then 2) keeping at 94° C. for 1 min, then at 50° C. for 2 min and at 75° C. for 3 min, for 20 times, and 2) keeping at 75° C. for 8 min. The thus-amplified DNA fragments may be amplified by PCR method, after purification as well as addition of the vector DNA comprising the wild-type gene having the nucleotide sequence of SEQ ID NO:2 and an oligonucleotide primer having the nucleotide sequence of SEQ ID NO:3. The thus-obtained DNA fragments may be digested with, for example, restriction endonucleases NcoI and XbaI, and ligated with the vector DNA comprising the wild-type reductase gene that have been similarly digested with the restriction endonucleases, to give the objective gene of the present invention.

The other amino acid that replaces the amino acid of the position 245 includes arginine and the like.

Furthermore, for example, in order to prepare the gene of the present invention that encodes the amino acid sequence of SEQ ID NO:1 with an amino acid substitution at amino acid position 271 using the method by Olfert Landt et al. (Gene 96 125–128 1990), the vector DNA comprising the wild-type gene having the nucleotide sequence of SEQ ID NO:2 is prepared first, for example, according to the methods described in J. Sambrook, E. F. Fritsch, T. Maniatis ed.; Molecular Cloning 2nd edition, Cold Spring Harbor Laboratory, 1989 and the like. Then the DNA fragment may be amplified by PCR method, using the obtained vector DNA as a template, for example, using an oligonucleotide comprising a nucleotide sequence that encodes the amino acid sequence of SEQ ID NO:1 with an amino acid substitution at the amino acid position 271 (e.g., an oligonucleotide having the nucleotide sequence of SEQ ID NO:7) as one primer and an oligonucleotide having the nucleotide sequence of SEQ ID NO:6 as the other primer. The condition of the PCR comprises, for example, 1) repeating a cycle comprising keeping at 94° C. for 5 min, then keeping at 94° C. for 1 min, at 50° C. for 2 min and at 75° C. for 3 min, for 20 times, and 2) keeping at 75° C. for 8 min. The thus-amplified DNA fragments may be amplified by PCR method, after purification as well as addition of the vector DNA comprising the wild-type gene having the nucleotide sequence of SEQ ID NO:2 and an oligonucleotide primer having the nucleotide sequence of SEQ ID NO:3. The thus-obtained DNA fragments may be digested with, for example, restriction endonuclease NcoI and XbaI, and ligated with the vector DNA comprising the wild-type gene that have been similarly digested with the restriction endonucleases, to give the objective gene of the present invention.

The other amino acid that replaces the amino acid of the position 271 includes aspartic acid and the like.

Of course, both of the amino acids at amino acid positions 245 and 271 of the amino acid sequence of SEQ ID NO:1 may be substituted with a same or different amino acid(s).

The specific examples of the gene of the present invention include, (a) a reductase having an amino acid sequence of SEQ ID NO:1 having a substitution of an amino acid at amino acid position 245 with arginine;

(b) a reductase having an amino acid sequence of SEQ ID NO:1 having a substitution of an amino acid at amino acid position 271 with aspartic acid;

(c) a reductase having an amino acid sequence of SEQ ID NO:1 having a substitution of an amino acid at amino acid position 245 with arginine and a substitution of an amino acid at amino acid position 271 with aspartic acid, and the like.

Using the thus-obtained gene of the present invention, the reductase of the present invention can be produced in a large amount and obtained according to a general method of gene engineering. Specifically, a transformant is prepared by, for example, preparing a vector that can express the gene of the present invention in a host cell of a microorganism and the like, and introducing the vector into a host cell and transforming the host cell. Then the transformed microorganism prepared as above may be cultivated according to a general cultivation method.

The above-mentioned vector can be constructed by introducing a vector that can be used in a host cell to which the gene of the present invention is introduced (hereinafter referred to as a basic vector), for example, a vector which comprises gene information capable of replicating in a host cell and can proliferate independently, can be isolated and purified from the host cell, and has a detectable marker, into the host cell, according to a general method of gene engineering.

As used herein, the "basic vector" specifically includes, when $E.\ coli$ is used as a host cell, such as vector pUC119 (manufactured by Takara Shuzo Co., Ltd.), phagemid pBluescript II (manufactured by Stratagene) and the like. When a bud yeast is used as a host cell, the basic vector includes such as vectors pGBT9, pGAD424, pACT2 (manufactured by Clonetech, Inc.)and the like. When a mammalian cell is used as a host cell, the basic vector includes vectors such as pRc/RSV, pRc/CMV (manufactured by Invitrogen Corporation) and the like, a vector comprising an autonomously replicating origin derived from viruses such as bovine papilloma virus vector pBPV (manufactured by Amarsham Pharmacia Biotech, Corp.) or EB virus vector pCEP4 (manufactured by Invitrogen Corporation), viruses such as vaccinia virus and the like. Furthermore, when an insect cell is used as a host cell, the basic vector includes insect viruses such as baculo virus and the like.

When the vector of the present invention is constructed with the vector comprising an autonomously replicating origin, such as the above-mentioned vector pACT2 for yeast, bovine papilloma virus vector pBPV, EB virus vector pCEP4 and the like, said vector is retained in a host cell as an episome when it is introduced in said cell.

The vector of the present invention may further comprise a polynucleotide having a nucleotide sequence that encodes the amino acid sequence of a protein capable of converting an oxidation-type β-nicotineamide adeninedinucleotide phosphate(NADP) or an oxidation-type β-nicotineamide adeninedinucleotide(NAD) into reduction-type(NADPH or NADH). By using such vector of the present invention, a transformant of the present invention further comprising a polynucleotide having a nucleotide sequence that encodes the amino acid sequence of a protein capable of converting an oxidation-type β-nicotineamide adeninedinucleotide phosphate or an oxidation-type β-nicotineamide adeninedinucleotide into reduction-type can be prepared.

The vector of the present invention capable of expressing the gene of the present invention in a host cell can be constructed by, binding a promoter capable of functioning in a host cell to the upstream of the gene of the present invention in functionable manner, and incorporating the gene in the above-mentioned basic vector. As used herein, "connecting in functionable manner" means, in a host cell to which the gene of the present invention is introduced, connecting a promoter with the gene of the present invention is conducted in such a manner that the gene of the present invention is expressed under the control of said promoter. The promoter capable of functioning in a host cell may include DNA that shows promoter activity in a host cell to which the promoter is introduced. For example, when the host cell is $E.\ coli$, the promoter includes such as a promoter of $E.\ coli$ lactose operon (lacP), a promoter of tryptophan operon (trpP), a promoter of arginine operon (argP), a promoter of galactose operon (galP), tac promoter, T7 promoter, T3 promoter, λ phage promoter (λ-pL, λ-pR) and the like. When the host cell is an animal cell or fission yeast, the promoter includes such as Rous sarcoma virus (RSV) promoter, cytomegalovirus (CMV) promoter, an early or late promoter of simian virus (SV40), mouse mammary tumor virus (MMTV) promoter and the like. When the host cell is bud yeast, the promoter includes ADH1 promoter and the like, which can be prepared from a yeast expression vector pAAH5 comprising the ADH1 promoter and ADH1 terminator [available from Washington Research Foundation, Ammerer et al., Method in Enzymology, 101 part (p. 192–201)] according to a general method of gene engineering. The ADH1 promoter is included in the U.S. patent application Ser. No. 299,733 assigned to the Washington Research Foundation, and when the promoter is used for industrial or commercial purpose, permission by the Assignee will be required.

When a basic vector that previously comprises a promoter that functions in a host cell is used, the gene of the present invention may be inserted in the downstream of the promoter so that the promoter is connected with the gene of the present invention in a functionable manner. For example, the above-mentioned vectors pRc/RSV, pRc/CMV and the like each contains a cloning site in the downstream of the promoter capable of functioning in an animal cell. By introducing the vector, which has been obtained by inserting the gene of the present invention in the cloning site, into an animal cell, the gene of the present invention can be expressed in the animal cell. Since these vectors already contain an autonomously replicating origin of SV40 (ori) when the vectors are introduced in a cultivated cell that has been transformed with an ori-deleted SV40 genome (e.g., COS cell and the like), the copy number of the vector is remarkably increased, which can result in the expression of the gene of the present invention, which has been incorporated in the vector, in a large amount. Furthermore, the above-mentioned vector pACT2 for yeast has an ADH1 promoter, and when the gene of the present invention is inserted in the downstream of the ADH1 promoter of said vector or a derivative thereof, the vector of the present invention that can express the gene of the present invention in a large amount in a bud yeast such as CG1945 (manufactured by Clontech, Inc.) and the like, can be constructed.

As the host cell, for example, when it is a microorganism, both eukaryote and prokaryote can be used, and the cell include such as E. coli and the like. The above-mentioned vector of the present invention can be introduced in the host cell according to a general method of gene engineering to transform the host cell.

As a method for introducing the vector of the present invention into a host cell, a general method for introduction, depending on the kind of the host cell, can be used. For example, when E. coli is used as a host cell, general methods such as calcium chloride method, electroporation method and the like as described in J. Sambrook, E. F. Frisch, T. Maniatis ed., Molecular Cloning 2nd Edition, Cold Spring Harbor Laboratory, 1989 and the like can be used. On the other hand, when a mammalian cell or insect cell is used as a host cell, the vector can be introduced according to general transgenic method such as calcium phosphate method, DEAE dextran method, electroporation method, lipofection method and the like. When yeast is used as a host cell, the introduction can be carried out using such as Yeast transformation kit (manufactured by Clontech, Inc.) based on lithium method, and the like.

When a virus is used as a vector, the genome of the virus can be introduced in a host cell according to the above-mentioned general transgenic method, or by infecting the host cell with virus particles comprising the genome of the virus in which the gene of the present invention has been inserted.

In order to screen the transformant of the present invention, for example, the host cell to which the vector of the present invention and a marker gene have been introduced may be cultivated according to various methods depending on the characteristic of the marker gene. For example, when the marker gene is a gene that provides drug tolerance for a screening agent having lethal activity for the host cell, the host cell to which the vector of the present invention have been introduced may be cultivated using a culture comprising the screening agent. The combination of a gene that provides drug tolerance and a screening agent includes combinations of a gene that provides neomycin-resistance and neomycin, a gene that provides hygromycin-resistance and hygromycin, a gene that provides blasticidin S-resistance and blasticidin S, and the like. Furthermore, when the marker gene is a gene that complements the auxotrophy of the host cell, the host cell to which the vector of the present invention have been introduced may be cultivated using a minimal medium that does not contain nutrients corresponding to the auxotrophy. When the vector of the present invention capable of expressing the gene of the present invention in a host cell is introduced, a detection method based on the enzyme activity of the reductase of the present invention may be used.

In order to obtain the transformant of the present invention in which the gene of the present invention is located in a chromosome of a host cell, for example, the vector of the present invention and a vector having a marker gene are digested with a restriction endonuclease and like and converted into a linear chain shape, and are then introduced in a host cell according to the above-mentioned method. The cell is then cultivated, generally for several weeks, and the objective transformant is screened and obtained based on the expression amount of the introduced marker gene. Alternatively, the transformant of the present invention to which the gene of the present invention has been introduced in a chromosome of a host cell can be screened and obtained by, for example, introducing the vector of the present invention having a gene that provides drug-resistance, as a marker gene, in a host cell, then sub-culturing the cell in a medium containing a screening agent for not less than several weeks, and purification cultivating the screening drug-resistant clone that has been survived in a colony shape. In order to confirm that the gene of the present invention has been included in the chromosome of the host cell, the existence of the gene of the present invention may be detected by, preparing the genomic DNA of said cell according to a general method of gene engineering, and subjecting the thus-prepared genomic DNA to a method such as PCR in which the DNA having the partial nucleotide sequence of the gene of the present invention is used as a primer or a probe, Southern hybridization and the like. Since the transformant can be preserved by cryo preservation and if required, can be defrosted before use, it can save the labor of preparation of transformant in each experiment, and a test can be carried out using the transformant in which its characteristic or handling condition have been confirmed.

The thus-obtained transformant comprising a vector comprising the gene of the present invention (hereinafter sometimes referred to as the transformant of the present invention) can be cultivated according to a general method of cell cultivation.

For example, when the transformant of the present invention is a microorganism, the transformant can be cultivated using various media that suitably includes carbon source, nitrogen source, organic or inorganic salts and the like, which are used in general cultivation of general microorganisms. For example, the carbon source includes sugars such as glucose, fructose, sucrose, dextrin and the like, sugar alcohols such as glycerol, sorbitol and the like, organic acids such as fumaric acid, citric acid and the like. The amount of the carbon source to be added to the medium may be generally about 0.1 to 10%. The nitrogen source includes ammonium salts of inorganic acid such as ammonium chloride, ammonium sulfate, ammonium phosphate and the like, ammonium salts of organic acid such as ammonium fumarate, ammonium citrate and the like, natural organic nitrogen sources such as meat extract, yeast extract, malt extract, soybean powder, corn steep liquor, cottonseed powder, dried yeast, casein hydrolysate and the like, amino acids and the like. Among these, many of the organic nitrogen sources can be used in combination with the carbon sources. The amount of the nitrogen source to be added to the medium may be generally about 0.1 to 10%. The inorganic salt includes such as alkaline metal phosphate such as potassium phosphate, sodium phosphate and the like, alkaline metal chloride such as potassium chloride, sodium chloride and the like, metal sulfate such as magnesium sulfate, ferrous sulfate and the like. The amount of the inorganic salt to be added to the medium is generally about 0.001 to 1%.

Additionally, the ability of the transformant of the present invention can be enhanced by previously adding a small amount of substrate, which is raw material, to a medium. The amount of the substrate to be added is usually about not less than 0.001%, preferably 0.1 to 1%.

The cultivation is conducted according to a general method for general microorganisms, and solid cultivation, liquid cultivation (revolving-type shaking cultivation, reciprocating-type shaking cultivation, jar fermenter cultivation, tank cultivation and the like) and the like may be used. Specifically, when a jar fermenter is used, introduction of sterilized air is necessary, and the condition for purging being used is about 0.1 to about 2 times/min of the amount of the cultivation solution. The temperature for cultivation and the pH of the medium can be suitably selected from the range in which the microorganism grows, and for example, the cultivation under the cultivation temperature of about 15° C. to about 40° C. and in a medium having the pH of about 6 to about 8 is preferred. While the period for cultivation varies depending on various conditions for cultivation, about one day to about five days is generally desired. When an expression vector having an inducible promoter such as temperature-shift type, IPTG inducible type and the like is used, the induction period is preferably within one day, generally several hours.

Alternatively, when the transformant is an animal cell such as mammalian cell, insect cell and the like, the transformant can be cultivated using media that are used in general cultivation of general culture cells. When the transformant is prepared using a screening agent, it is preferable to cultivate the transformant in the presence of the screening agent. In the case of mammalian cell, it may be cultivated using a DMEM medium (manufactured by Nissui Co,. Ltd. and the like) in which FBS has been added so that the final concentration is adjusted to 10%, at 37° C. and in the presence of 5% $CO_2$, with changing the cultivation solution every several days. When the cells have been proliferated and become confluent, for example, PBS solution in which trypsin has been added so that the concentration is adjusted to about 0.25 (w/v), is added thereto to disperse the cells, the solution is diluted by several folds and inoculated to a new dish, and the cultivation is continued. In the case of insect cell, similarly, for example, the cell may cultivated at the cultivation temperature of 25° C. to 35° C. using a cultivation solution for insect cell, such as Grace's medium comprising 10% (v/v) PBS and 2% (w/v) Yeastlate, and the like. During the cultivation, when the cell is easy to exfoliate from the dish, such as Sf21 cell and the like, passage cultivation may be carried out without using trypsin solution and with dispersing by pipetting. When a transformant comprising a virus vector of baculovirus and the like is used, the cultivation is preferably finished until the cytoplasmic effect is expressed and the cells are killed, for example, up to 72 hours after the infection with the virus.

The thus-obtained transformant of the present invention that produces the reductase of the present invention or a treated transformant thereof can be used for such as an organic synthetic reaction for production of compounds used as active ingredients of medicaments or agrochemicals (for example, 4-halo-3-oxobutyrate ester) or intermediates thereof, especially optically active compounds or intermediates thereof, as a bioreactor that reduces a substrate.

The treated material of the transformant of the present invention includes the cultivated transformant of the present invention that has been obtained by cultivating as above, for example, the transformant of the present invention itself, a cultivation solution containing the transformant of the present invention, or a treated transformant such as an insoluble transformant in which sterilized cells that have been sterilized by physical sterilization (heating, drying, freezing, ray, ultrasonic, filtration, applying an electric current) or chemical sterilization (alkali, acid, halogen, oxidizing agent, sulfur, boron, arsenic, metal, alcohol, phenol, amine, sulfide, ether, aldehyde, ketone, cyanide, antibiotic) and the like, lyophilized cells, acetone-dried cells, crushed cells, autolyzed cell, cells treated with ultrasonic, cell extract, crude purified enzyme, purified enzyme, or treated transformant, has been immobilized by a known method such as polyacrylic amide method, sulfur-containing polysacchalide method (for example, carrageenan gel method), arginic acid gel method, agar gel method and the like.

As mentioned above, the reductase of the present invention is collected and purified from the cultivated transformant that has been obtained by cultivating the transformant of the present invention, and which can be used as an enzyme reactor. The collection and purification of the reductase from the cultivated transformant of the present invention can be carried out by suitably combining general methods for extraction, isolation and purification for protein. For example, the collection and purification of the reductase of the present invention may be carried out by, for example, collecting the cultivated transformant of the present invention by centrifugation and the like, crushing or bacteriolysing, and using various chromatography methods such as ion exchange, hydrophobic, gel permeation and the like. Furthermore, as mentioned above, the transformant of the present invention or the reductase of the present invention may be immobilized onto a suitable carrier, and which can be used as a reactor.

By reacting the transformant of the present invention or a treated material of the transformant with 4-halo-3-oxobutyrate ester, for example, (S)-4-halo-3-hydroxybutyrate ester can be prepared.

The above-mentioned 4-halo-3-oxobutyrate ester is an ester of formula 1:

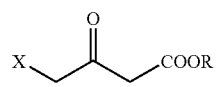

wherein X is chlorine atom, bromine atom or iodine atom, and R is an alkyl group, an aryl group or a substituted group thereof. The alkyl group as R of the ester of the general formula 1 is preferably a lower alkyl group having 1 to 8 carbon atom(s)(e.g. methyl, ethyl, propyl, butyl, pentyl, hexyl, heptyl octyl and the like).

Specifically, the ester includes, for example, methyl 4-chloro-3-oxobutyrate, ethyl 4-chloro-3-oxobutyrate, propyl 4-chloro-3-oxobutyrate, methyl 4-bromo-3-oxobutyrate, ethyl 4-bromo-3-oxobutyrate, propyl 4-bromo-3-oxobutyrate, octyl 4-bromo-3-oxobutyrate and the like.

The reaction is usually carried out in the presence of water and reduction-type nicotineamide adeninedinucleotide phosphate (hereinafter referred to as NADPH). The water used in the reaction may be an aqueous buffer solution. The buffering agent used for the aqueous buffer solution includes alkaline metal phosphates such as sodium phosphate, potassium phosphate and the like, alkaline metal acetates such as sodium acetate, potassium acetate and the like, or a mixture thereof.

During the above-mentioned reaction, an organic solvent may exist besides water. The organic solvent that may exist includes ethers such as t-butyl methyl ether, diisopropyl ether, tetrahydrofuran and the like, esters such as ethyl formate, ethyl acetate, propyl acetate, butyl acetate, ethyl propionate, butyl propionate and the like, hydrocarbons such as toluene, hexane, cyclohexane, heptane, isooctane and the like, alcohols such as methanol, ethanol, 2-propanol, butanol, t-butylalcohol and the like, organic sulfur compound such as dimethylsulfoxide, ketones such as acetone and the like, nitrites such as acetonitrile and the like, or a mixture thereof.

The reaction in the above-mentioned method is usually carried out by, for example, mixing water, NADPH and 4-halo-3-oxobutyrate ester with the transformant of the present invention or a treated material thereof, optionally in the presence of an organic solvent and the like, by stirring, shaking and the like.

While the pH for the reaction in the above-mentioned method can be suitably selected, the pH is usually 3 to 10. While the temperature for the reaction can be suitably selected, the temperature is usually in the range of 0 to 60° C., in view of stability of raw materials and product and reaction velocity.

The reaction can be monitored by, for example, tracing the amount of 4-halo-3-oxobutyrate ester in the reaction solution using liquid chromatography and the like. While the reaction time can be suitably selected, the time is usually in the range of 0.5 hr to 10 days.

The collection of the (S)-4-halo-3-hydroxybutyrate ester may be carried out by any of the generally known methods.

For example, purification may be conducted, for example by a post-treatment such as extraction of the reaction solution with an organic solvent, concentration and the like, optionally in combination with column chromatography, distillation and the like.

The present invention also relates to: a method for modifying an enzyme, characterized in that the method comprises replacing at least one of the amino acid residues 245 and 271 in the amino acid sequence of SEQ ID NO:1, with another amino acid(s), so as to improve the optical purity of the reaction product or cognition of said enzyme to the absolute configuration of a substrate in the reduction reaction in which said enzyme functions as a catalyst; and a production method for a modified enzyme gene, characterized in that the method comprises replacing a codon of at least one of the amino acid residues 245 and 271 of an amino acid sequence of SEQ ID NO:1, with a codon of another amino acid(s), in the nucleotide sequence encoding the amino acid sequence of SEQ ID NO:1.

EXAMPLES

Hereinafter the present invention is explained in more detail with referring to the Preparation Examples, which do not limit the present invention.

Example 1

Preparation of a gene of a wild-type reductase, which is a template DNA (1-1) Preparation of a cDNA library A medium (a solution of potato dextrose broth (manufactured by Becton Dickinson and Company) in water, 24 g/L) (100 ml) was put into a 500 ml flask and sterilized at 121° C. for 15 min. The thus-prepared medium was inoculated with a cultivation solution of *Penicillium citrinum* IFO4631 strain (available from the Institute for Fermentation, Osaka (www.ifo.or.jp)), which solution had been previously cultivated in a liquid culture having the above-mentioned composition (30° C., 48 hr, cultivated with shaking) (0.5 ml), and cultivated at 30° C. for 72 hr with shaking.

After cultivation, the obtained cultivation solution was centrifuged (8000×g, 10 min) to collect bacterial cells as precipitate. The collected bacterial cells were washed three times with 20 mM monopotassium phosphate-dipotassium phosphate buffer (pH 7.0) (50 ml) to give wet bacterial cells (about 1.0 g).

The whole RNA was prepared from the thus-obtained wet bacterial cells using guanidium thiocyanate-phenol-chloroform method. An RNA having poly (A) was obtained from the thus-prepared whole RNA using Oligotex (dT) 30-Super (manufactured by Takara Shuzo Co., Ltd.).

The cDNA library was prepared according to the Gubler and Hoffman method. Firstly, a single-stranded cDNA was prepared using the thus-obtained RNA having poly (A), Oligo (dT) 18-linker primer (XhoI-containing site, manufactured by Takara Shuzo Co., Ltd.), RAV-2 Rtase and Super Script II Rtase. To the prepared single-stranded cDNA (the reaction solution containing the cDNA) were added *E. coli* DNA polymerase, *E. coli* Rnase/*E. coli* DNA Ligase Mixture and T4 DNA Polymerase to synthesize a double-stranded cDNA, which was then subjected to blunt-ending.

The thus-obtained double-strand cDNA and an EcoRI-NotI-BamHI adaptor (manufactured by Takara Shuzo Co., Ltd.) were subjected to ligation. The DNA obtained by the ligation was subjected to phosphorylation treatment, cleavage treatment with XhoI, and treatment for removing low molecular weight DNA with a spin column (manufactured by Takara Shuzo Co., Ltd.), and ligated with λ ZapII (cleavage of EcoRI-XhoI) and packaged using an in vitro packaging kit (manufactured by STRATAGENE Corporation) to prepare a cDNA library (hereinafter also referred to as cDNA library (A)).

(1-2) Preparation of a vector comprising a wild-type reductase gene (construction of vector pTrcRPc)

PCR was carried out using an oligonucleotide having the base sequence of SEQ ID NO:3 and an oligonucleotide having the base sequence of SEQ ID NO:4 as primers, and using the cDNA library prepared in the above-mentioned (1-1) as a template, at the following composition and reaction condition (using the Expand High Fidelity PCR system, manufactured by Roche Diagnostic Systems Inc.)

| Composition of the reaction solution | |
|---|---|
| cDNA library stock solution | 1 μl |
| dNTP (each 2.5 mM-mix) | 0.4 μl |
| Primer (20 pmol/μl) | Each 0.75 μl |
| 10x buffer (with MgCl$_2$) | 5 μl |
| enz. expand HiFi (3.5 × 10$^3$ U/ml) | 0.375 μl |
| Ultrapure water | 41.725 μl |

Reaction Condition

A vessel containing the reaction solution having the above-mentioned composition was set in the PERKIN ELMER-GeneAmp PCR System 2400 and heated to 97° C. (2 min). Then a cycle of 97° C. (0.25 min)–55° C. (0.5 min)–72° C. (1.5 min) was repeated 10 times, a cycle of 97° C. (0.25 min)–55° C. (0.5 min)–72° C. (2.5 min) was repeated 20 times, and the vessel was kept at 72° C. for 7 min.

To the PCR amplified DNA fragment that had been obtained by the purificarion of the PCR reaction solution were added two kinds of restriction endonucleases (NcoI and BamHI) to double digest the DNA fragment. The obtained DNA fragment was then purified.

On the other hand, two kinds of restriction endonucleases (NcoI and BamHI) were added to the vector pTrc99A (manufactured by Pharmacia Corporation) to double digest the vector. The digested DNA fragment was then purified.

The thus-obtained two DNA fragments were mixed and ligated with T4 DNA ligase. *E. coli* DH5α was transformed with the obtained ligation solution. A vector comprising a wild-type reductase gene (hereinafter also referred to as vector pTrcRPc) was taken from the obtained transformant using QIAprep Spin Miniprep Kit (manufactured by Qiagen Genomics, Inc.).

Example 2

Preparation of a Gene of a Coenzyme-regenerating Gene (2-1) Preparation for the Preparation of a Gene having a Base Sequence that Encodes an Amino Acid Sequence of an Enzyme Capable of Converting an Oxydation-type β-nicotineamide Adenine Dinucleotide, etc. into Reduction-type An LB medium (1% trypton, 0.5% yeast extract, 1% sodium chloride) (100 ml) was put into a 500 ml flask and sterilized at 121° C. for 15 min. The thus-prepared medium was inoculated with a cultivation solution of Bacillus megaterium IF012108 strain that had been previously cultivated in a liquid medium having the above-mentioned composition (30° C., 48 hr, cultivated with shaking) (0.3 ml), and cultivated at 30° C. for 10 hr with shaking.

After cultivation, the obtained cultivation solution was centrifuged (8000×g, 10 min, 4° C.) to collect bacterial cells as precipitate. The collected bacterial cells were washed three times with 50 mM phosphate monopotassium-phosphate dipotassium buffer (pH 7.0) (30 ml) to give wet bacterial cells (about 0.4 g).

A chromosome DNA was purified from the thus-obtained wet bacterial cells using Qiagen Genomic Tip (manufactured by Qiagen Genomics, Inc.) according to the method described in a manual attached thereto.

(2-2) Preparation of a Gene having a Base Sequence that Encodes an Amino Acid Sequence of an Enzyme Capable of Converting an Oxydation-type β-nicotineamide Adenine Dinucleotide, etc. into Reduction-type (Construction of Vector pTrcGDH12)

An oligonucleotide having the base sequence of SEQ ID NO:8 (including NcoI) and an oligonucleotide having the base sequence of SEQ ID NO:9 (including BamHI) are synthesized based on the amino acid sequence of the glucose dehydrogenase derived from the known Bacillus megaterium IWG3 described in the Journal of Biological Chemistry Vol. 264, No. 11, 6381–6385 (1989).

PCR is carried out using the oligonucleotide having the base sequence of SEQ ID NO:8 (including NcoI) and oligonucleotide having the base sequence of SEQ ID NO:9 (including BamHI) as primers, and using the chromosome DNA prepared in the above-mentioned (2-1) as a template, at the composition of the reaction solution and reaction condition described in the Example 1 (1-2) (using Expand High Fidelity PCR system, manufactured by Roche Diagnostic Systems Inc.) To the PCR amplified DNA fragment, which has been obtained by purification of the PCR reaction solution, are added two kinds of restriction endonucleases (NcoI and BamHI) to double digest the DNA fragment. The obtained DNA fragment is then purified.

On the other hand, two kinds of restriction endonucleases (NcoI and BamHI) are added to the vector pTrc99A (manufactured by Pharmacia Corporation) to double digest the vector. The digested DNA fragment is then purified.

The thus-obtained two DNA fragments are mixed and ligated with T4 DNA ligase. *E. coli* HB101 strain is transformed with the obtained ligation solution. A vector comprising a gene having a base sequence that encodes an amino acid sequence of an enzyme capable of converting an oxydation-type β-nicotineamide adeninedinucleotide etc. into reduction-type (hereinafter also referred to as vector pTrcGDH12) is taken from the obtained transformant using QIAprep Spin Miniprep Kit (manufactured by Qiagen Genomics, Inc.)

Example 3

Preparation of the Gene of the Present Invention: Introduction of Site-specific Mutagenesis (3-1) Operation for Introduction of Site-specific Mutagenesis Based on the base sequence of SEQ ID NO:2, various synthetic oligonucleotides (mutation primers) that correspond to each amino acids were synthesized as mutation primers for converting the amino acids of the positions 245 and 271 into the other amino acids, as represented in SEQ ID NOs: 5 and 7.

PCR was carried out using oligonucleotides having the base sequences of SEQ ID NOs: 5 and 7 and an oligonucleotide having the base sequence of SEQ ID NO:6 as primers, and using the vector pTrcRPc purified in the above-mentioned (1-2) as a template, at the following composition and reaction condition (using Expand High Fidelity PCR system, manufactured by Roche Diagnostic Systems Inc.). The obtained PCR reaction solution is referred to as PCR reaction solution (A). Furthermore, PCR was carried out using an oligonucleotide having the base sequence of SEQ ID NO:10 and an oligonucleotide having the base sequence of SEQ ID NO:11 as primers, and using the vector pTrcRPc purified in the above-mentioned (1-2) as a template, at the following composition of the reaction solution of the reaction solution and reaction condition (using Expand High Fidelity PCR system, manufactured by Roche Diagnostic Systems Inc.) The obtained PCR reaction solution is referred to as PCR reaction solution (B).

| Composition of the reaction solution | |
|---|---|
| pTrcRPc vector solution | 1 μl |
| dNTP (each 2.5 mM-mix) | 0.4 μl |
| Primer (20 pmol/μl) | Each 0.75 μl |
| 10x buffer (with $MgCl_2$) | 5 μl |
| enz. expand HiFi ($3.5 \times 10^3$ U/ml) | 0.375 μl |
| Ultrapure water | 41.725 μl |

PCR Reaction Condition

A vessel containing the reaction solution having the above-mentioned composition was set in the PERKIN ELMER-GeneAmp PCR System 2400. A cycle of 94° C. (0.5 min)–55° C. (2 min)–72° C. (1.5 min) was repeated 25 times and the vessel was kept at 4° C.

The PCR reaction solution (A) and PCR reaction solution (B) were purified respectively, and the resulting two PCR amplified DNA fragments were mixed and heat-denaturated. After the denaturation, they were gradually cooled and annealed. To the fragments were added enz. expand HiFi to complete a heteroduplex, and an oligonucleotide having the base sequence of SEQ ID NO:10 and an oligonucleotide having the base sequence of SEQ ID NO:6 were added thereto as primers. PCR was carried out at the following reaction condition (using Expand High Fidelity PCR system, manufactured by Roche Diagnostic Systems Inc.)

PCR Reaction Condition

A vessel containing the reaction solution having the above-mentioned composition was set in the PERKIN ELMER-GeneAmp PCR System 2400. A cycle of 94° C. (0.5 min)–55° C. (2 min)–72° C. (1.5 min) was repeated 10 times and the vessel was kept at 4° C.

The PCR reaction solution was purified and two kinds of restriction endonucleases (NcoI and PstI) were added thereto to double digest the PCR amplified fragment. The obtained DNA fragment was then purified.

On the other hand, two kinds of restriction endonucleases (NcoI and PstI) were added to the vector pTrc99A to double digest the vector. The digested DNA fragment was then purified.

The thus-obtained two DNA fragments were mixed and ligated with T4 DNA ligase. E. coli HB101 strain was transformed with the obtained ligation solution.

(3-2) Screening of Mutant

A vector was extracted from the transformant obtained in the (3-1), and the base sequence of the mutated site was determined by dideoxy method to confirm that the designed mutation had been introduced. The operations of the above-mentioned (3-1) and (3-2) were conducted in a similar manner for a mutant in which the lysine of the position 245 and asparagine of the position 271 had been replaced, to give transformants of each mutant plasmids (vectors of the present invention, K245R, N271D).

Example 4

Preparation of a Multiply-mutated Gene of the Present Invention (4-1) Operation for Introduction of Site-specific Mutagenesis PCR is carried out using an oligonucleotide having the base sequence of SEQ ID NO:7 and an oligonucleotide having the base sequence of SEQ ID NO:6 as primers, and using the vector K245R purified in the above-mentioned (3-2) as a template, at the following composition of the reaction solution and reaction condition (using Expand High Fidelity PCR system, manufactured by Roche Diagnostic Systems Inc.). The obtained PCR reaction solution is referred to as PCR reaction solution (C).

Furthermore, PCR is carried out using an oligonucleotide having the base sequence of SEQ ID NO:10 and an oligonucleotide having the base sequence of SEQ ID NO:11 as primers, and using the vector K245R purified in the above-mentioned (3-2) as a template, at the following composition of the reaction solution and reaction condition (using Expand High Fidelity PCR system, manufactured by Roche Diagnostic Systems Inc.) The obtained PCR reaction solution is referred to as PCR reaction solution (D).

| Composition of the reaction solution | |
|---|---|
| Template vector solution | 1 μl |
| dNTP (each 2.5 mM-mix) | 0.4 μl |
| Primer (20 pmol/μl) | Each 0.75 μl |
| 10x buffer (with $MgCl_2$) | 5 μl |
| enz. expand HiFi ($3.5 \times 10^3$ U/ml) | 0.375 μl |
| Ultrapure water | 41.725 μl |

PCR Reaction Condition

A vessel containing the reaction solution having the above-mentioned composition is set in the PERKIN ELMER-GeneAmp PCR System 2400. A cycle of 94° C. (0.5 min)–55° C. (2 min)–72° C. (1.5 min) was repeated 25 times and the vessel was kept at 4° C.

The PCR reaction solution (C) and PCR reaction solution (D) are purified respectively, and the resulting two PCR amplified DNA fragments are mixed and heat-denaturated. After the denaturation, they are gradually cooled and annealed. To the fragments are added enz. expand HiFi to complete a heteroduplex, and an oligonucleotide having the base sequence of SEQ ID NO:10 and an oligonucleotide having the base sequence of SEQ ID NO:6 are added thereto as primers. PCR is carried out at the following reaction condition (using Expand High Fidelity PCR system, manufactured by Roche Diagnostic Systems Inc.)

PCR Reaction Condition

A vessel containing the reaction solution having the above-mentioned composition is set in the PERKIN ELMER-GeneAmp PCR System 2400. A cycle of 94° C.

(0.5 min)–55° C. (2 min)–72° C. (1.5 min) was repeated 10 times and the vessel was kept at 4° C.

The PCR reaction solution is purified and two kinds of restriction endonucleases (NcoI and PstI) are added thereto to double digest the PCR amplified fragment. The digested DNA fragment is then purified.

On the other hand, two kinds of restriction endonucleases (NcoI and PstI) are added to the vector pTrc99A to double digest the vector. The digested DNA fragment is then purified.

The thus-obtained two DNA fragments were mixed and ligated with T4 DNA ligase. E. coli HB101 strain is transformed with the obtained ligation solution.

(4-2) Screening of Mutant

A vector is extracted from the transformant obtained in the (4-1), and the base sequence of the mutated site is determined by dideoxy method to confirm that the designed mutation has been introduced. The transformant of a multiply-mutated vector (multiple mutated vector of the present invention, K245RN271D) is obtained.

Example 5

Preparation of a Transformant Comprising the Gene of the Present Invention and a Gene of a Coenzyme-regenerating Enzyme (Construction of Vectors pTrcGK245R and pTrcGN271D)

Based on the base sequence of SEQ ID NO:2 (a base sequence of a gene of a wild-type reductase), an oligonucleotide having the base sequence of SEQ ID NO: 12 (including BamHI) and an oligonucleotide having the base sequence of SEQ ID NO:13 (including XbaI) were synthesized.

PCR was carried out using the oligonucleotide having the base sequence of SEQ ID NO: 12 (including BamHI) and oligonucleotide having the base sequence of SEQ ID NO:13 (including XbaI) as primers, and using the vector DNA comprising the mutated reductase gene purified in the above-mentioned (3-2) or (4-2) as a template, at the following composition of the reaction solution and reaction condition (using the Expand High Fidelity PCR system, manufactured by Roche Diagnostic Systems Inc.)

| Composition of the reaction solution | |
|---|---|
| Vector solution | 1 µl |
| dNTP (each 2.5 mM-mix) | 0.4 µl |
| Primer (20 pmol/µl) | Each 0.75 µl |
| 10x buffer (with MgCl₂) | 5 µl |
| enz. expand HiFi (3.5 × 10³ U/ml) | 0.375 µl |
| Ultrapure water | 41.725 µl |

PCR Reaction Condition

A vessel containing the reaction solution having the above-mentioned composition was set in the PERKIN ELMER-GeneAmp PCR System 2400 and heated to 97° C. (2 min). Then a cycle of 97° C. (0.25 min)–55° C. (0.5 min)–72° C. (1.5 min) was repeated 10 times, a cycle of 97° C. (0.25 min)–55° C. (0.5 min)–72° C. (2.5 min) was repeated 20 times, and the vessel was kept at 72° C. for 7 min.

To a PCR amplified DNA fragment obtained by purifying the PCR reaction solution were added two kinds of restriction endonucleases (BamHI and XbaI) to double digest the DNA fragments. The obtained DNA fragments were then purified.

On the other hand, two kinds of restriction endonucleases (BamHI and XbaI) were added to the pTrcGDH12 vector DNA to double digest the vector. The digested DNA fragments were then purified.

The thus-obtained two DNA fragments were mixed and ligated with T4 DNA ligase. E. coli DH5α was transformed with the obtained ligation solution. A vector comprising a wild-type reductase gene or a mutated reductase gene (hereinafter also referred to as vectors pTrcGK245R, pTrcGN271D, pTrcGK245RN271D) was taken from the obtained transformant using a QIAprep Spin Miniprep Kit (manufactured by Qiagen Genomics, Inc.)

Example 6

Heat-stability of the Enzyme of the Present Invention

Each of the three transformants obtained in Example 3 or 4 was inoculated in a sterilized LB culture (100 ml) containing IPTG (0.1 mM) and ampicillin (50 µg/ml), and cultivated with shaking at 30° C. for 12 hr. After the cultivation, the obtained cultivation solution was centrifuged (8000×g, 10 min) to collect wet bacterial cells as precipitate. To the collected bacterial cells (about 0.4 g) was added 0.1 M phosphate buffer (pH 6.5) (20 ml) and the mixture was crushed using glass beads. The crushed solution was centrifuged (12000×g, 10 min) to give supernatant, which was used as a crude enzyme solution.

A test liquid having the protein concentration of the crude enzyme solution of 0.05 mg/ml was kept at 45° C. for 7 hr, and the residual activity of the reductase of the present invention was determined. Methyl 4-bromo-3-oxobutyrate was used as a substrate for determination of the activity. Specifically, methyl 4-bromo-3-oxobutyrate (1.56 mg), the crude enzyme solution (100 µl), NADPH (0.208 mg) and 100 mM phosphate buffer (pH 6.5) (0.9 ml) were mixed. The mixture was kept at 30° C., and the decreasing amount of NADPH was measured as decrease of the absorbance at 220 nm. The activity of the reductase was of a unit, which was the amount of the enzyme that oxidizes 1 µmol of NADPH per minute. The results are shown in Table 1.

TABLE 1

| Reductase of the present invention | Residual activity (%) |
|---|---|
| K245R | 3.2 |
| N271D | 6.8 |
| Wild type reductase (comparative control) | 0 |

As used herein, for example, the "N245D" represents the reductase of the present invention in which the asparagine at the position 245 (N) has been replaced with aspartic acid (D).

Example 7

Preparation of the Transformant of the Present Invention and Reduction Reaction

E. coli HB101 is transformed using the vector N271D or K245R. Each of the obtained transformant is inoculated in a sterilized LB culture (100 ml) containing IPTG (0.1 mM) and ampicillin (50 µg/ml), and cultivated with shaking at 30° C. for 12 hr. After the cultivation, the obtained cultivation solution is centrifuged (8000×g, 10 min) to collect wet bacterial cells as precipitate. The wet bacterial cells (about 0.4 g) are obtained.

Methyl 4-bromo-3-oxobutyrate (300 mg), the above-mentioned wet bacterial cells (0.4 g), NADP+ (9 mg), glucose (750 mg), glucose dehydrogenase (manufactured by Amano Pharmaceuticals, Co., Ltd.) (1.2 mg), 100 mM phosphate buffer (pH 6.5) (15 ml) and butyl acetate (15 ml) are mixed. The mixture is stirred at 30° C. for 7 hr. During the stirring, 2M aqueous sodium carbonate solution is gradually added to adjust the pH of the reaction solution to 6.5±0.2. After the stirring has been finished, the reaction solution is centrifuged (1000×g, 5 min) to collect the organic layer. The organic layer is subjected to an analysis for content using gas chromatography under the following condition. The optical purity of methyl 4-bromo-3-hydroxybutyrate in the above-mentioned organic layer was also determined under the following condition. The organic layer was concentrated to give crude methyl (S)-4-bromo-3-hydroxybutyrate.

Condition for Analysis of Content
Column: HR-20M (0.53 mm×30 m, 1 μm) (manufactured by Shinwa Kako Co., Ltd.)
Column temperature: 120° C. (5 min)→3° C./min→150° C. (5 min)→10° C./min→200° C. (5 min)
Carrier gas: helium (flow rate: 20 ml/min)
Detector: FID Condition for Determination of Optical Purity
Column: G-TA (0.25 mm×30 m, 0.125 μm) (manufactured by Astech, Co., Ltd.)
Column temperature: 110° C. (20 min)→5° C./min→180° C. (1 min)
Carrier gas: helium (flow rate: 1 ml/min)
Detector: FID
Split ratio: 1/50

The absolute configuration of the reaction product was determined by comparing with the sample of methyl (S)4-bromo-3-hydroxybutyrate.

Example 8

Production of the Reductase of the Present Invention Using Transformants

The three transformants obtained in Example 3 or 4 were inoculated in an LB culture (50 ml) containing IPTG (0.1 mM) and ampicillin (100 μg/ml), and cultivated with shaking at 30° C. for 12 hr. After the cultivation, the obtained cultivation solution was centrifuged (8000×g, 10 min) to collect bacterial cells as precipitate. A part of the collected bacterial cells (corresponding to 5 μl of the cultivated solution) were subjected to SDS-PAGE. For all of the three samples, a protein was observed as a major band at the position corresponding to the molecular weight of the wild-type reductase.

Example 9

Purification of the Reductase of the Present Invention

Each of the three transformants cultivated according to the method of Example 8 is crushed by ultrasonic (20 KHz, 15 min, 4° C.) and centrifuged (100000×g, 60 min, 4° C.) to give supernatant. To the obtained ultracentrifuged supernatant (150 ml) is added ammonium sulfate until its concentration reaches to 1.5 M. The solution is spread on a hydrophobic interaction chromatography column [Hi-Load Phenyl (26/10) (manufactured by Amersham Pharmacia Biotech, Inc.)] [equilibrated with BIS-TRIS-PROPANE buffer containing 1.5 M ammonium sulfate (20 mM, pH 7.0)], and the objective enzyme is eluted using BIS-TRIS-PROPANE buffer including ammonium sulfate (having concentration gradient of ammonium sulfate of 1.5 M→0.6 M) as a mobile phase. The determination of the activity of the enzyme for the eluted fraction is carried out using 4-halo-3-oxobutyrate ester, which is a substrate for reductase.

Specifically, a phosphate buffer including methyl 4bromo-3-oxo-butyrate (1.56 mg/ml) and NADPH (0.226 mg/ml) (20 mM, pH 7.0, 0.9 ml) is added to the eluant including the eluted fraction (0.1 ml), and the mixture is kept at 30° C., and the increase of the absorbance at 340 nm is measured. The fraction having the activity of the reductase is collected, desalted and replaced with Tris-HCl buffer (20 mM, pH 7.7). The fraction is spread on an ion exchange chromatography column [Hi-Load Q Sepharose (16/10) (manufactured by Amersham Pharmacia Biotech, Inc.)] [equilibrated with Tris-HCl buffer (20 mM, pH 7.7)], and the objective enzyme is eluted using Tris-HCl buffer including sodium chloride (having concentration gradient of sodium chloride of 0→0.5 M) as a mobile phase. The fraction having the activity of the reductase is collected to give the purified reductase.

EFFECT OF THE INVENTION

According to the present invention, there is provided a reductase having good heat stability, which resulted in decrease in reaction time and improvement of reaction efficiency, said reductase can be suitably used for an organic synthesis reaction for producing compounds used as active ingredients of medicaments or agrochemicals or intermediates thereof, especially for producing optically active compounds or intermediates thereof having good optical purity.

What is claimed is:

1. An isolated β-keto acid reductase comprising the amino acid sequence of SEQ ID NO:1 except that: the amino acid at amino acid position 245 is substituted with arginine, the amino acid at amino acid position 271 is substituted with aspartic acid, or both the amino acids at amino acid position 245 and 271 are substituted with arginine and aspartic acid, respectively.

2. A method for modifying a β-keto acid reductase, which consists of substituting one of the amino acid at positions 245 or 271 of the amino acid sequence of SEQ ID NO:1 with another amino acid, wherein the amino acid at position 245 is substituted with arginine and the amino acid at amino acid position 271 is substituted with aspartic acid and wherein the modified β-keto acid reductase continues to have β-keto acid reductase activity.

* * * * *

SEQUENCE LISTING

<160> NUMBER OF SEQ ID NOS: 13

<210> SEQ ID NO 1
<211> LENGTH: 325
<212> TYPE: PRT
<213> ORGANISM: Penicillium citrinum

<400> SEQUENCE: 1

Met Ser Asn Gly Lys Thr Phe Thr Leu Ser Asn Gly Val Lys Ile Pro
 1               5                  10                  15

Gly Val Gly Phe Gly Thr Phe Ala Ser Glu Gly Ser Lys Gly Glu Thr
            20                  25                  30

```
Tyr Thr Ala Val Thr Thr Ala Leu Lys Thr Gly Tyr Arg His Leu Asp
             35                  40                  45

Cys Ala Trp Tyr Tyr Leu Asn Glu Gly Glu Val Gly Glu Gly Ile Arg
 50                  55                  60

Asp Phe Leu Lys Glu Asn Pro Ser Val Lys Arg Glu Asp Ile Phe Val
 65                  70                  75                  80

Cys Thr Lys Val Trp Asn His Leu His Arg Tyr Glu Asp Val Leu Trp
                 85                  90                  95

Ser Ile Asp Asp Ser Leu Lys Arg Leu Gly Leu Asp Tyr Val Asp Met
            100                 105                 110

Phe Leu Val His Trp Pro Ile Ala Ala Glu Lys Asn Gly Gln Gly Glu
            115                 120                 125

Pro Lys Ile Gly Pro Asp Gly Lys Tyr Val Ile Leu Lys Asp Leu Thr
            130                 135                 140

Glu Asn Pro Glu Pro Thr Trp Arg Ala Met Glu Lys Ile Tyr Glu Asp
145                 150                 155                 160

Arg Lys Ala Arg Ser Ile Gly Val Ser Asn Trp Thr Ile Ala Asp Leu
                165                 170                 175

Glu Lys Met Ser Lys Phe Ala Lys Val Met Pro His Ala Asn Gln Ile
                180                 185                 190

Glu Ile His Pro Phe Leu Pro Asn Glu Glu Leu Val Gln Tyr Cys Phe
            195                 200                 205

Ser Lys Asn Ile Met Pro Val Ala Tyr Ser Pro Leu Gly Ser Gln Asn
            210                 215                 220

Gln Val Pro Thr Thr Gly Glu Arg Val Ser Glu Asn Lys Thr Leu Asn
225                 230                 235                 240

Glu Ile Ala Glu Lys Gly Asn Thr Leu Ala Gln Val Leu Ile Ala
                245                 250                 255

Trp Gly Leu Arg Arg Gly Tyr Val Val Leu Pro Lys Ser Ser Asn Pro
            260                 265                 270

Lys Arg Ile Glu Ser Asn Phe Lys Ser Ile Glu Leu Ser Asp Ala Asp
            275                 280                 285

Phe Glu Ala Ile Asn Ala Val Ala Lys Gly Arg His Phe Arg Phe Val
            290                 295                 300

Asn Met Lys Asp Thr Phe Gly Tyr Asp Val Trp Pro Glu Glu Thr Ala
305                 310                 315                 320

Lys Asn Leu Ser Ala
            325

<210> SEQ ID NO 2
<211> LENGTH: 978
<212> TYPE: DNA
<213> ORGANISM: Penicillium citrinum
<220> FEATURE:
<221> NAME/KEY: CDS
<222> LOCATION: (1)..(975)

<400> SEQUENCE: 2 atg tct aac gga aag act ttc aca ttg agc aac ggc gtc aag att cct      48
Met Ser Asn Gly Lys Thr Phe Thr Leu Ser Asn Gly Val Lys Ile Pro
 1               5                  10                  15 ggc gtc ggc ttt ggt acc ttc gct agt gaa ggt tcc aag ggc gag acc      96
Gly Val Gly Phe Gly Thr Phe Ala Ser Glu Gly Ser Lys Gly Glu Thr
             20                  25                  30 tat act gct gtc acc act gcc ctg aag acc ggt tac cgt cac ttg gac     144
Tyr Thr Ala Val Thr Thr Ala Leu Lys Thr Gly Tyr Arg His Leu Asp
```

```
                35                  40                  45
tgt gcc tgg tac tac ctg aac gag ggt gag gtt ggt gag ggt atc cgt    192
Cys Ala Trp Tyr Tyr Leu Asn Glu Gly Glu Val Gly Glu Gly Ile Arg
     50                  55                  60 gac ttc ctg aag gag aac ccc tcg gtg aag cgt gag gac atc ttc gtc    240
Asp Phe Leu Lys Glu Asn Pro Ser Val Lys Arg Glu Asp Ile Phe Val
 65                  70                  75                  80 tgc acc aag gtg tgg aac cac ctc cac cgt tat gag gac gtc ctc tgg    288
Cys Thr Lys Val Trp Asn His Leu His Arg Tyr Glu Asp Val Leu Trp
                 85                  90                  95 tcc att gac gac tcc ctg aag cgt ctt gga ctt gac tac gtt gat atg    336
Ser Ile Asp Asp Ser Leu Lys Arg Leu Gly Leu Asp Tyr Val Asp Met
            100                 105                 110 ttc ctc gtt cac tgg ccc att gct gcc gag aag aat ggc cag ggt gag    384
Phe Leu Val His Trp Pro Ile Ala Ala Glu Lys Asn Gly Gln Gly Glu
        115                 120                 125 ccc aag att ggc cct gac ggc aaa tac gtc att ctc aag gac ctg acc    432
Pro Lys Ile Gly Pro Asp Gly Lys Tyr Val Ile Leu Lys Asp Leu Thr
130                 135                 140 gag aac ccc gag ccc aca tgg cgc gct atg gag aag att tat gag gat    480
Glu Asn Pro Glu Pro Thr Trp Arg Ala Met Glu Lys Ile Tyr Glu Asp
145                 150                 155                 160 cgc aag gcc agg tcc att ggt gtc tcc aac tgg acc att gcc gac ctt    528
Arg Lys Ala Arg Ser Ile Gly Val Ser Asn Trp Thr Ile Ala Asp Leu
                165                 170                 175 gag aag atg tcc aag ttc gcc aag gtc atg cct cac gcc aac cag atc    576
Glu Lys Met Ser Lys Phe Ala Lys Val Met Pro His Ala Asn Gln Ile
            180                 185                 190 gag att cac ccc ttc ctg ccc aac gag gag ctg gtg cag tac tgc ttc    624
Glu Ile His Pro Phe Leu Pro Asn Glu Glu Leu Val Gln Tyr Cys Phe
        195                 200                 205 tcc aag aac att atg ccc gtg gcc tac tct cct ctg ggc tcg cag aac    672
Ser Lys Asn Ile Met Pro Val Ala Tyr Ser Pro Leu Gly Ser Gln Asn
210                 215                 220 cag gtt ccc acc acc ggt gag cgg gtc agc gag aac aag act ctg aac    720
Gln Val Pro Thr Thr Gly Glu Arg Val Ser Glu Asn Lys Thr Leu Asn
225                 230                 235                 240 gag atc gcc gag aag ggc ggc aac acc ctt gct cag gtt ctt att gcc    768
Glu Ile Ala Glu Lys Gly Gly Asn Thr Leu Ala Gln Val Leu Ile Ala
                245                 250                 255 tgg ggt ctg cgc cgt ggc tac gtc gtt ctc ccc aag agc tcc aac ccc    816
Trp Gly Leu Arg Arg Gly Tyr Val Val Leu Pro Lys Ser Ser Asn Pro
            260                 265                 270 aag cgc att gag tcc aac ttc aag agc att gag ctc tcc gat gcc gac    864
Lys Arg Ile Glu Ser Asn Phe Lys Ser Ile Glu Leu Ser Asp Ala Asp
        275                 280                 285 ttt gaa gcc atc aat gcc gtt gcc aag ggt cgt cac ttc cgt ttc gtc    912
Phe Glu Ala Ile Asn Ala Val Ala Lys Gly Arg His Phe Arg Phe Val
290                 295                 300 aac atg aag gat act ttc gga tat gat gtc tgg ccc gag gag acc gcc    960
Asn Met Lys Asp Thr Phe Gly Tyr Asp Val Trp Pro Glu Glu Thr Ala
305                 310                 315                 320 aag aac ctg tct gcg tga                                            978
Lys Asn Leu Ser Ala
                325

<210> SEQ ID NO 3
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      PCR primer

<400> SEQUENCE: 3
gccatggcta tgtctaacgg aaagact                                          27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 4
cggatccgtt cacgcagaca ggttcttgg                                        29

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 5
gagaggggcg gcaacaccct t                                                21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 6
ggctgaaaat cttctctcat                                                  20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7
tccgacccca agcgcattga g                                                21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
gccatggcta tgtataaaga tttagaa                                          27

<210> SEQ ID NO 9
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      PCR primer

<400> SEQUENCE: 9
cggatccgtt atccgcgtcc tgc                                              23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
tgttgacaat taatcatccg                                                  20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 11
aagcttgcat gccttcgggt cgac                                             24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 12
cggatccgag gaaacagacc atgg                                             24

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
ctctagagtt ataatttcgt agagattca                                        29
```